United States Patent [19]

Mark et al.

[11] 4,273,942

[45] Jun. 16, 1981

[54] PLASTICIZED POLYCARBONATE COMPOSITION

[75] Inventors: Victor Mark, Evansville, Ind.; Phillip S. Wilson, Louisville, Ky.

[73] Assignee: General Electric Company, Pittsfield, Mass.

[21] Appl. No.: 158,647

[22] Filed: Jun. 12, 1980

Related U.S. Application Data

[60] Division of Ser. No. 37,922, May 9, 1979, which is a continuation-in-part of Ser. No. 957,353, Nov. 3, 1978, abandoned, which is a division of Ser. No. 781,054, Mar. 24, 1977, Pat. No. 4,184,994.

[51] Int. Cl.$^3$ .............................................. C07C 49/76
[52] U.S. Cl. ................................. 568/42; 260/32.8 R; 260/30.8 R
[58] Field of Search ..................... 260/32.8; 568/42, 54

[56] References Cited

U.S. PATENT DOCUMENTS

| | | | |
|---|---|---|---|
| 2,999,835 | 9/1961 | Goldberg | 568/42 |
| 3,028,365 | 4/1962 | Schnell | 568/42 |
| 3,097,138 | 7/1963 | Cavallini et al. | 568/42 |
| 3,150,187 | 9/1964 | Cavallini et al. | 568/42 |
| 3,169,121 | 2/1965 | Goldberg | 568/47 |
| 3,334,154 | 8/1967 | Kim | 260/860 |
| 4,082,807 | 4/1978 | Eiglmeier | 568/42 |
| 4,184,994 | 1/1980 | Mark et al. | 260/32.8 |

*Primary Examiner*—Werren B. Lone
*Attorney, Agent, or Firm*—William F. Mufatti

[57] ABSTRACT

A plasticized polycarbonate composition comprising in admixture a high molecular weight aromatic carbonate polymer and a minor amount of an organic plasticizer.

1 Claim, No Drawings

PLASTICIZED POLYCARBONATE COMPOSITION

This application is a division of copending application Ser. No. 37,922 filed May 9, 1979 which, in turn, is a continuation-in-part application of prior, copending application Ser. No. 957,353 filed Nov. 3, 1978, now abandoned, which, in turn, is a division of prior, copending application Ser. No. 781,054 filed Mar. 24, 1977, now U.S. Pat. No. 4,184,994.

This invention is directed to a plasticized polycarbonate composition comprising in admixture a high molecular weight aromatic carbonate polymer and a minor amount of a particular organic plasticizer.

BACKGROUND OF THE INVENTION

Polycarbonate polymers are excellent molding materials as products made therefrom have high impact strength, toughness, high transparency, wide temperature limits (high impact resistance below $-60°$ C. and a UL thermal endurance rating of 115° C. with impact), good dimensional stability, high creep resistance and electrical properties which qualify it as sole support for current carrying parts.

Polycarbonates are, however, very difficult to fabricate from melts for the reason that melts thereof have exceptionally high viscosities. Attempts to overcome this difficulty by the incorporation with the polycarbonate of materials known to reduce the viscosity of other resins have very generally been unsuccessful. Many standard viscosity control agents appear to have little or no effect on the viscosity of polycarbonate. Other compounds known to lower the viscosity of resins cause degradation of polycarbonate resins. Some compounds, conventionally employed to improve the workability of polymers, produce an embrittling effect on polycarbonates when they are mixed therewith and the resin is subjected to elevated temperatures as in molding. Still other materials, while satisfactory stiffness modifying agents for other plastics, are too volatile to be incorporated with polycarbonates since polycarbonates have much higher melting points than many other thermoplastics.

DESCRIPTION OF THE INVENTION

It has been surprisingly discovered that, by admixing a minor amount of a particular organic plasticizer with a high molecular weight aromatic carbonate polymer, the resultant polycarbonate composition has reduced melt viscosity and does not become brittle or degraded upon molding and thus retains its characteristic high impact strength.

In the practice of this invention, the organic plasticizer additive is selected from those represented by the following general formula:

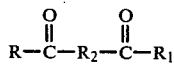

wherein R and $R_1$ are independently selected from the group consisting of $C_1$ to $C_{30}$ alkyl, aryl of 6 to 14 carbon atoms and substituted aryl wherein the substituents on said substituted aryl are $C_1$ to $C_{30}$ alkyl, halogen, $C_1$ to $C_{30}$ alkoxy, aryloxy of 6 to 14 carbon atoms, alkylthio of 1 to 30 carbon atoms and arylthio of 6 to 14 carbon atoms; $R_2$ is $C_1$ to $C_{30}$ alkylene, arylene of 6 to 14 carbon atoms, alkarylene of 7 to 30 carbon atoms, aralkylene of 7 to 30 carbon atoms and

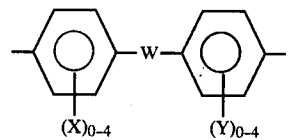

wherein W is selected from the group consisting of:
(a) —O—;
(b) —S—;

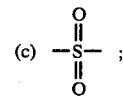

wherein X and Y are independently selected from the group consisting of halogen and $C_1$–$C_{12}$ alkyl.

These plasticizers are prepared by methods well known in the art. For example, these ketones may be prepared by methods as set forth in Morrison and Boyd, *Organic Chemistry*, Allyn and Bacon, Inc. (Boston), 1963, Chapter 23, pages 617 to 644.

The amount of organic plasticizer employed in the practice of this invention may vary from 0.05 to about 5.0 parts per hundred parts of aromatic carbonate polymer. Preferably, these organic plasticizers are employed in amounts of from 0.25 to 2.0 parts per hundred parts of aromatic carbonate polymer.

In the practice of this invention, the high molecular weight aromatic polycarbonates that can be employed herein are homopolymers and copolymers and mixtures thereof which have an I.V. of 0.40 to 1.0 dl/g as measured in methylene chloride at 25° C. that are prepared by reacting a dihydric phenol with a carbonate precursor. Typical of some of the dihydric phenols that may be employed in the practice of this invention are bisphenol-A, [2,2-bis(4-hydroxyphenyl) propane], bis(4-hydroxyphenyl) methane, 2,2-bis(4-hydroxy-3methylphenyl) propane, 4,4-bis(4-hydroxyphenyl) heptane, 2,2-(3,5,3',5'-tetrachloro-4,4'-dihydroxydiphenyl) propane, 2,2-(3,5,3',5'-tetrabromo-4,4'-dihydroxydiphenyl) propane, (3,3'-dichloro-4,4'-dihydroxydiphenyl) methane. Other dihydric phenols of the bisphenol type are also available and are disclosed in U.S. Pat. Nos. 2,999,835, 3,028,365 and 3,334,154.

It is, of course, possible to employ two or more different dihydric phenols or a copolymer of a dihydric phenol with a glycol or with hydroxy or acid terminated polyester, or with a dibasic acid in the event a carbonate copolymer or inter-polymer rather than a homopolymer is desired for use in the preparation of the aromatic carbonate polymers of this invention. Also employed in the practice of this invention may be blends of any of the above materials to provide the aromatic carbonate polymer.

The carbonate precursor may be either a carbonyl halide, a carbonate ester or a haloformate. The carbonyl halides which can be employed herein are carbonyl bromide, carbonyl chloride and mixtures thereof. Typical of the carbonate esters which may be employed herein are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonates such as di(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates suitable for use herein include bis-haloformates of dihydric phenols (bischloroformates) of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The aromatic carbonate polymers of this invention may be prepared by employing a molecular weight regulator, an acid acceptor and a catalyst. The molecular weight regulators which can be employed in carrying out the process of this invention include monohydric phenols such as phenol, chroman-I, paratertiarybutylphenol, parabromophenol, primary and secondary amines, etc. Preferably, phenol is employed as the molecular weight regulator.

A suitable acid acceptor may be either an organic or an inorganic acid acceptor. A suitable organic acid acceptor is a tertiary amine and includes such materials as pyridine, triethylamine, dimethylaniline, tributylamine, etc. The inorganic acid acceptor may be one which can be either a hydroxide, a carbonate, a bicarbonate, or a phosphate of an alkali or alkaline earth metal.

The catalysts which are employed herein can be any of the suitable catalysts that aid the polymerization of bisphenol-A with phosgene. Suitable catalysts include tertiary amines such as, for example, triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethylammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

Also included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds which may be employed in the practice of this invention include: trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride and the like. The preferred polyfunctional aromatic compounds are trimellitic anhydride or trimellitic acid or their haloformyl derivatives.

Also, included herein are blends of a linear polycarbonate and a branched polycarbonate.

The composition of the instant invention is prepared by blending the high molecular weight aromatic polycarbonate with the additive by conventional methods.

Obviously, other materials can also be employed with the aromatic carbonate polymer of this invention and include such materials as anti-static agents, pigments, thermal stabilizers, ultraviolet stabilizers, reinforcing fillers and the like.

PREFERRED EMBODIMENT OF THE INVENTION

In order to more fully and clearly illustrate the present invention, the following specific examples are presented. It is intended that the examples be considered as illustrative rather than limiting the invention disclosed and claimed herein. In the examples, all parts and percentages are on a weight basis unless otherwise specified.

EXAMPLE 1

One hundred (100) parts of an aromatic polycarbonate, prepared from 2,2-bis(4-hydroxyphenyl) propane and phosgene in the presence of an acid acceptor and a molecular weight regulator and having an intrinsic viscosity of about 0.57, is mixed with the additive listed in the Table by tumbling the ingredients together in a laboratory tumbler. The resulting mixture is then fed to an extruder which is operated at about 265° C., and the extrudate is comminuted into pellets.

The pellets are then fed into a plastometer and the flow rate of the polymer is measured according to ASTM D1238-70, Condition O. The melt flow rate is set forth in the Table.

Additionally, the pellets are injection molded at about 315° C. into test specimens of about 5 by ½ by ⅛ inch thick. The impact strength of these specimens is then measured according to the Izod test, ASTM D256. The impact strength is set forth in the Table. The sample labeled CONTROL is the polycarbonate as prepared without additive.

In the Table, the additive, 4,4'-di(hexadecanoyl)diphenyl ether, having the structure:

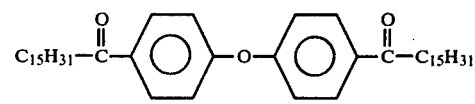

was prepared in accordance with the method described in Journal of Polymer Science, Part A-1, 1972, pp. 2919–23.

The novel additive, 4,4'-di(hexadecanoyl)diphenyl sulfide, having the structure:

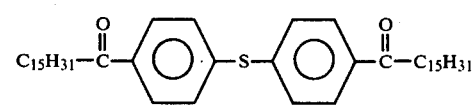

was prepared by the Friedel-Crafts acylation of diphenyl sulfide with 2 moles of hexadecanoyl chloride and an excess of aluminum chloride in carbon disulfide solution. Purification of the crude product by recrystallization from benzene produced the 4,4'-isomer, the structure of which was confirmed by the presence of two doublets in the aromatic region of the proton nmr spectrum.

TABLE

| Additive | Amount of Additive (Parts per Hundred) | Melt Flow Rate (gr./10 min.) | Impact Strength (Ft. Lbs./In.) |
| --- | --- | --- | --- |
| CONTROL | — | 10.10 | 15.0 |
| 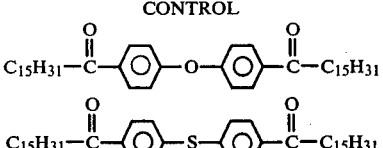 | 1.0 | 16.32 | 15.8 |
| 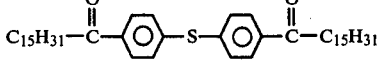 | 0.5 | 12.90 | 16.5 |

It can be seen from the data in the Table that when the instant organic plasticizer is added to a high molecular weight aromatic polycarbonate, the resulting polycarbonate composition has reduced melt viscosity as shown by the higher melt flow rate while retaining impact strength.

It will thus be seen that the objects set forth above among those made apparent from the preceding description are efficiently attained and since certain changes may be made in carrying out the above process and in the composition set forth without departing from the scope of this invention, it is intended that all matters contained in the above description shall be interpreted as illustrative and not in a limiting sense.

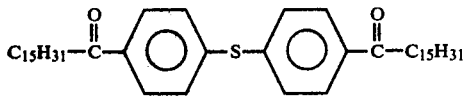

What is claimed is:

1. A novel compound having the formula: